(12) United States Patent
Munch-Fals et al.

(10) Patent No.: US 7,868,221 B2
(45) Date of Patent: Jan. 11, 2011

(54) ELECTRO ACTIVE ELASTIC COMPRESSION BANDAGE

(75) Inventors: Jakob Munch-Fals, Virum (DK); Mohamed Yahia Benslimane, Nordborg (DK); Peter Gravesen, Nordborg (DE); Theiss Stenstroem, Soenderborg (DK)

(73) Assignee: Danfoss A/S, Nordborg (DK)

( * ) Notice: Subject to any disclaimer, the term of this patent is extended or adjusted under 35 U.S.C. 154(b) by 559 days.

(21) Appl. No.: 10/546,514

(22) PCT Filed: Feb. 24, 2004

(86) PCT No.: PCT/DK2004/000123
§ 371 (c)(1),
(2), (4) Date: Oct. 20, 2005

(87) PCT Pub. No.: WO2004/093763
PCT Pub. Date: Nov. 4, 2004

(65) Prior Publication Data
US 2006/0079824 A1    Apr. 13, 2006

(30) Foreign Application Priority Data
Feb. 24, 2003   (DK) ................................ 2003 00277

(51) Int. Cl.
*A61F 13/00*   (2006.01)
(52) U.S. Cl. .......................................................... 602/41
(58) Field of Classification Search ............. 602/41–56, 602/60, 75
See application file for complete search history.

(56) References Cited

U.S. PATENT DOCUMENTS 2,130,532 A    9/1938  Bailey
2,716,708 A    8/1955  Bradfield
3,109,202 A   11/1963  Beckadolph et al.

(Continued)

FOREIGN PATENT DOCUMENTS

DE          30 06 620 A1    9/1981

(Continued)

OTHER PUBLICATIONS

Publication "High-field electrostriction of elastomeric polymer dielectrics for actuation" by Roy Kornbluh, et al., SRI International; SPIE vol. 3669, pp. 149-161; Mar. 1999.

(Continued)

*Primary Examiner*—Michael A. Brown
(74) *Attorney, Agent, or Firm*—McCormick, Paulding & Huber LLP

(57) ABSTRACT

This invention relates to an elastic bandage for supporting a body extremity such as a leg. Such bandages are used to overcome problems with fluid retention and swelling in the legs, occurring as a consequence of varicose veins, vascular incompetence, pregnancy, etc. It is a task of this invention to supply an active support for a body extremity such as a leg, which can be used by a person underneath the clothes and will not reduce the mobility of the patient. This task is solved in that an elastic bandage comprises an elastic layer for surrounding a body extremity to exert compressive force on the extremity, the bandage being, at least partly, formed by elastomeric actuation elements, whereby electrical control of the compressive force is possible, and where the control is due to a signal from some sensing system.

10 Claims, 2 Drawing Sheets

U.S. PATENT DOCUMENTS

| | | | |
|---|---|---|---|
| 3,138,962 A | 6/1964 | Haines, Jr. et al. | |
| 3,544,733 A | 12/1970 | Reylek | |
| 3,565,195 A | 2/1971 | Miller et al. | 177/210 |
| 3,753,294 A | 8/1973 | Attali et al. | 33/133 |
| 3,831,629 A * | 8/1974 | Mackal et al. | 137/843 |
| 3,875,481 A | 4/1975 | Miller et al. | 317/246 |
| 3,898,585 A | 8/1975 | Heidrich et al. | |
| 3,912,830 A | 10/1975 | Murayama et al. | |
| 4,259,607 A | 3/1981 | Noguchi et al. | |
| 4,266,263 A | 5/1981 | Haberl et al. | 361/283 |
| 4,322,877 A | 4/1982 | Taylor | |
| 4,330,730 A | 5/1982 | Kurz et al. | 310/331 |
| 4,370,697 A | 1/1983 | Haberl et al. | 361/283 |
| 4,376,302 A | 3/1983 | Miller | 367/157 |
| 4,384,394 A | 5/1983 | Lemmonon et al. | 29/25.35 |
| 4,386,386 A | 5/1983 | Akita | 361/283 |
| 4,431,882 A | 2/1984 | Frame | 200/5 |
| 4,494,409 A | 1/1985 | Kondo et al. | 73/651 |
| 4,549,093 A | 10/1985 | Severwright | |
| 4,634,917 A | 1/1987 | Dvorsky et al. | 310/328 |
| 4,640,137 A | 2/1987 | Trull et al. | |
| 4,654,546 A | 3/1987 | Kirjavainen | 307/400 |
| 4,731,694 A | 3/1988 | Grabner et al. | 361/280 |
| 4,825,116 A | 4/1989 | Itoh et al. | 310/335 |
| 4,829,812 A | 5/1989 | Parks et al. | 73/12 |
| 4,836,033 A | 6/1989 | Seitz | 73/862.04 |
| 4,852,443 A | 8/1989 | Duncan et al. | 84/1.04 |
| 4,866,412 A | 9/1989 | Rzepczynski | 338/114 |
| 4,879,698 A | 11/1989 | Langberg | 367/140 |
| 4,986,136 A | 1/1991 | Brunner et al. | 73/862.04 |
| 5,048,536 A | 9/1991 | McEwen | 128/748 |
| 5,060,527 A | 10/1991 | Burgess | 73/862.68 |
| 5,090,246 A | 2/1992 | Colla et al. | 73/718 |
| 5,090,248 A | 2/1992 | Cimmino et al. | 73/780 |
| 5,115,680 A | 5/1992 | Lew | 73/763 |
| 5,172,024 A | 12/1992 | Broussoux et al. | |
| 5,173,162 A | 12/1992 | Hagimura et al. | 204/299 |
| 5,255,972 A | 10/1993 | Shirasu | 60/528 |
| 5,259,099 A | 11/1993 | Banno et al. | |
| 5,300,813 A | 4/1994 | Joshi et al. | |
| 5,321,332 A | 6/1994 | Toda | 310/322 |
| 5,325,012 A | 6/1994 | Sato et al. | |
| 5,341,062 A | 8/1994 | Cero, Jr. et al. | |
| 5,410,210 A | 4/1995 | Sato et al. | 310/363 |
| 5,425,275 A | 6/1995 | Lockshaw | 73/775 |
| 5,447,076 A | 9/1995 | Ziegler | 73/862.626 |
| 5,449,002 A | 9/1995 | Goldman | 128/779 |
| 5,494,090 A | 2/1996 | Kejha | |
| 5,515,341 A | 5/1996 | Toda et al. | |
| 5,520,630 A | 5/1996 | Daneshvar | 602/60 |
| 5,528,452 A | 6/1996 | Ko | 361/283.4 |
| 5,548,564 A | 8/1996 | Smith | 367/140 |
| 5,559,387 A | 9/1996 | Beurrier | |
| 5,642,015 A | 6/1997 | Whitehead et al. | |
| 5,755,909 A | 5/1998 | Gailus | 156/229 |
| 5,817,099 A * | 10/1998 | Skolik et al. | 606/107 |
| 5,841,143 A | 11/1998 | Tuma et al. | 250/458.1 |
| 5,888,646 A | 3/1999 | Takahashi et al. | |
| 5,891,065 A * | 4/1999 | Cariapa et al. | 601/152 |
| 5,977,685 A | 11/1999 | Kurita et al. | 310/311 |
| 5,997,465 A | 12/1999 | Savage et al. | 600/20 |
| 6,008,580 A | 12/1999 | Nakamura et al. | |
| 6,008,582 A | 12/1999 | Asano et al. | |
| 6,108,175 A | 8/2000 | Hawwa et al. | |
| 6,123,681 A | 9/2000 | Brown, III | 602/75 |
| RE37,065 E | 2/2001 | Grahn | 73/628 |
| 6,208,065 B1 | 3/2001 | Ueyama | |
| 6,210,514 B1 | 4/2001 | Cheung et al. | 156/241 |
| 6,216,495 B1 | 4/2001 | Couzan et al. | 66/183 |
| 6,255,758 B1 | 7/2001 | Cabuz et al. | |
| 6,282,956 B1 | 9/2001 | Okada | 73/504.12 |
| 6,343,129 B1 | 1/2002 | Pelrine et al. | 381/191 |
| 6,376,971 B1 | 4/2002 | Pelrine et al. | 310/363 |
| 6,411,015 B1 | 6/2002 | Toda | |
| 6,437,489 B1 | 8/2002 | Shinke et al. | 310/369 |
| 6,543,110 B1 | 4/2003 | Pelrine et al. | 29/25.35 |
| 6,545,384 B1 | 4/2003 | Pelrine et al. | 310/309 |
| 6,545,395 B2 | 4/2003 | Matsui et al. | 310/369 |
| 6,581,481 B1 | 6/2003 | Perusek | 73/862.337 |
| 6,583,533 B2 | 6/2003 | Pelrine et al. | 310/309 |
| 6,586,859 B2 | 7/2003 | Kornbluh et al. | 310/309 |
| 6,628,040 B2 | 9/2003 | Pelrine et al. | 310/307 |
| 6,662,658 B2 | 12/2003 | Foote | 73/514.29 |
| 6,664,718 B2 | 12/2003 | Pelrine et al. | 310/800 |
| 6,700,304 B1 | 3/2004 | Fuller et al. | |
| 6,700,312 B2 | 3/2004 | Iizuka et al. | |
| 6,707,236 B2 | 3/2004 | Pelrine et al. | 310/800 |
| 6,759,769 B2 | 7/2004 | Kirjavainen | |
| 6,768,246 B2 | 7/2004 | Pelrine et al. | 310/339 |
| 6,781,284 B1 | 8/2004 | Pelrine et al. | 310/330 |
| 6,806,621 B2 | 10/2004 | Heim et al. | 310/328 |
| 6,809,462 B2 | 10/2004 | Pelrine et al. | 310/800 |
| 6,812,624 B1 | 11/2004 | Pei et al. | 310/800 |
| 6,876,135 B2 | 4/2005 | Pelrine et al. | 310/339 |
| 6,882,086 B2 | 4/2005 | Kornbluh et al. | 310/328 |
| 6,891,317 B2 | 5/2005 | Pei et al. | 310/800 |
| 6,911,764 B2 | 6/2005 | Pelrine et al. | 310/328 |
| 6,940,211 B2 | 9/2005 | Pelrine et al. | 310/330 |
| 7,034,432 B1 | 4/2006 | Pelrine et al. | 310/309 |
| 7,049,732 B2 | 5/2006 | Pei et al. | 310/800 |
| 7,064,472 B2 | 6/2006 | Pelrine et al. | 310/324 |
| 7,104,146 B2 | 9/2006 | Benslimane et al. | 73/862.626 |
| 7,211,937 B2 | 5/2007 | Kornbluh et al. | |
| 7,518,284 B2 | 4/2009 | Benslimane et al. | |
| 7,548,015 B2 | 6/2009 | Benslimane et al. | |
| 7,573,064 B2 | 8/2009 | Benslimane et al. | |
| 2001/0026165 A1 | 10/2001 | Pelrine et al. | 324/750 |
| 2001/0035723 A1 | 11/2001 | Pelrine et al. | 318/116 |
| 2002/0008445 A1 | 1/2002 | Pelrine et al. | 310/330 |
| 2002/0041017 A1 | 4/2002 | Hauser et al. | |
| 2002/0050768 A1 | 5/2002 | Beck et al. | 310/334 |
| 2002/0130673 A1 | 9/2002 | Pelrine et al. | 324/727 |
| 2002/0175594 A1 | 11/2002 | Kornbluh et al. | 310/317 |
| 2002/0175598 A1 | 11/2002 | Heim et al. | 310/328 |
| 2002/0185937 A1 | 12/2002 | Heim et al. | 310/339 |
| 2003/0006669 A1 | 1/2003 | Pei et al. | 310/309 |
| 2003/0066741 A1 | 4/2003 | Burgess et al. | 200/61.43 |
| 2003/0067245 A1 | 4/2003 | Pelrine et al. | 310/311 |
| 2003/0125781 A1 | 7/2003 | Dohno et al. | 607/75 |
| 2003/0141473 A1 | 7/2003 | Pelrine et al. | 251/129.06 |
| 2003/0141787 A1 | 7/2003 | Pelrine et al. | 310/365 |
| 2003/0213960 A1 | 11/2003 | Kitagawa et al. | |
| 2003/0214199 A1 | 11/2003 | Heim et al. | 310/309 |
| 2004/0008853 A1 | 1/2004 | Pelrine et al. | 381/191 |
| 2004/0012301 A1 | 1/2004 | Benslimane et al. | 310/311 |
| 2004/0056567 A1 | 3/2004 | Menzel | |
| 2004/0124738 A1 | 7/2004 | Pelrine et al. | 310/307 |
| 2004/0217671 A1 | 11/2004 | Rosenthal et al. | 310/328 |
| 2004/0232807 A1 | 11/2004 | Pelrine et al. | 310/800 |
| 2004/0263028 A1 | 12/2004 | Pei et al. | 310/800 |
| 2005/0040736 A1 | 2/2005 | Topliss et al. | 310/367 |
| 2005/0104145 A1 | 5/2005 | Benslimane et al. | 257/415 |
| 2005/0157893 A1 | 7/2005 | Pelrine et al. | 381/190 |
| 2006/0016275 A1 | 1/2006 | Gravesen et al. | 73/862.042 |
| 2006/0066183 A1 | 3/2006 | Benslimane et al. | 310/369 |
| 2006/0079824 A1 | 4/2006 | Munch-Fals et al. | |
| 2006/0113878 A1 | 6/2006 | Pei et al. | 310/363 |
| 2006/0113880 A1 | 6/2006 | Pei et al. | 310/800 |
| 2006/0119225 A1 | 6/2006 | Heim et al. | 310/339 |
| 2006/0158065 A1 | 7/2006 | Pelrine et al. | 310/328 |
| 2007/0114885 A1 | 5/2007 | Benslimane et al. | |
| 2007/0116858 A1 | 5/2007 | Benslimane et al. | |
| 2007/0269585 A1 | 11/2007 | Benslimane et al. | |
| 2007/0277356 A1 | 12/2007 | Benslimane et al. | |

| | | | |
|---|---|---|---|
| 2008/0038860 A1 | 2/2008 | Benslimane et al. | |
| 2008/0093954 A1 | 4/2008 | Benslimand et al. | |
| 2008/0226878 A1 | 9/2008 | Benslimane et al. | |
| 2008/0238258 A1 | 10/2008 | Ishiguro et al. | |
| 2008/0265709 A1 | 10/2008 | Clausen et al. | |
| 2009/0064476 A1 | 3/2009 | Cross et al. | |
| 2009/0072658 A1 | 3/2009 | Benslimane et al. | |
| 2009/0169829 A1 | 7/2009 | Benslimane et al. | |
| 2009/0239039 A1 | 9/2009 | Benslimane et al. | |

FOREIGN PATENT DOCUMENTS

| | | |
|---|---|---|
| DE | 30 23 218 A1 | 2/1982 |
| DE | 38 41 243 A1 | 6/1990 |
| DE | 198 26 391 A1 | 12/1999 |
| DE | 200 04 248 U1 | 8/2000 |
| DE | 100 54 247 A1 | 5/2002 |
| DE | 100 54 247 C2 | 5/2002 |
| EP | 0 387 180 A1 | 9/1990 |
| EP | 0 421 368 B1 | 4/1991 |
| EP | 0 761 188 A2 | 3/1997 |
| EP | 0 855 307 B1 | 3/2003 |
| EP | 1 324 403 A1 | 7/2003 |
| EP | 148 1738 A2 | 12/2004 |
| FR | 2 309 833 | 12/1976 |
| FR | 2 793 937 A1 | 11/2000 |
| GB | 2042256 A | 9/1980 |
| JP | 55-42474 | 3/1980 |
| JP | 55-91299 | 7/1980 |
| JP | 1-273372 | 11/1989 |
| JP | 2002-237625 | 8/2003 |
| JP | 2005-117103 | 4/2005 |
| JP | 2007-11206 A | 1/2007 |
| JP | 2008-205180 A | 9/2009 |
| KR | 90-1465 | 3/1990 |
| WO | WO 96/34701 | 11/1996 |
| WO | WO 97/27822 | 8/1997 |
| WO | WO 00/66970 | 11/2000 |
| WO | WO 01/06575 A1 | 1/2001 |
| WO | WO 01/06579 A2 | 1/2001 |
| WO | WO 01/58973 A2 | 8/2001 |
| WO | WO 01/59852 A3 | 8/2001 |
| WO | WO 01/63738 A2 | 8/2001 |
| WO | WO 01/65615 A3 | 9/2001 |
| WO | WO 02/37660 A1 | 5/2002 |
| WO | WO 2004/079832 A2 | 9/2004 |
| WO | WO 2005/079187 A2 | 9/2005 |
| WO | WO 2005/081676 A2 | 9/2005 |

OTHER PUBLICATIONS

Publication Micro-Electro-Mechanical Systems (MEMS)—2000-; by R. Trujillo, et al.; Presented at 2000 ASIME International Mechanical Engineering Congress and Exposition, Nov. 5-10, 2000; Orland, FL; pp. 709-716.

International Search Report for Serial No. PCT/DK03/00603 dated Feb. 5, 2004.

PCT Search Report for Serial No. PCT/DK03/00848 dated Mar. 25, 2004.

Article entitled "Electrostrictive Polymer Artificial Muscle Actuators" by R. Kornbluh, et al., SRI International, Proceedings of the 1998 IEEE International Conference on Robotics & Automation, Belgium, May 1998; pp. 2147-2154.

Article entitled "Spontaneous formation of ordered structures in thin films of metals supportd on an elastomeric polymer" by Ned Bowden, et al., Nature, vol. 393, May 14, 1998; pp. 149-149.

Article entitled "Silicone Elastomers with Controlled Surface Composition Using Argon or Hydrogen Plasma Treatment" by B. Orlander, et al., Journal of Applied Polymer Science, vol. 90, 2003 Wiley Periodicals, Inc.; pp. 1378-1383.

* cited by examiner

ELECTRO ACTIVE ELASTIC COMPRESSION BANDAGE

CROSS REFERENCE TO RELATED APPLICATIONS

This application is entitled to the benefit of and incorporates by reference essential subject matter disclosed in International Patent Application No. PCT/DK2004/000123 filed on Feb. 24, 2004 and Danish Patent Application No. PA 2003 00277 filed Feb. 24, 2003.

FIELD OF THE INVENTION

This invention relates to an elastic bandage for supporting a body extremity such as a leg. Such bandage are used to overcome problems with fluid retention and swelling in the legs, occurring as a consequence of Varicose veins, vascular incompetence, pregnancy, etc.

BACKGROUND OF THE INVENTION

Supporting stockings used to overcome the described problems are known in a lot of variations, and are on the market in a lot of models and sizes. However, they are all passive, meaning that they are produced with a given elasticity that will decrease over time. Typically, support stockings can be used for about 6 months, whereafter they have lost the major part of their elasticity.

Support stockings that are inflatable are also known, and they are able to add a well-adjusted compressive force to a body extremity such as a leg. A pneumatic device inflates each compartment in the stocking to a given level of pressure, and this pressure is maintained for a given period. This type of stockings is, however, only useable in a controlled environment, like a hospital or in the home of a permanently sick person, and is only to be used during periods where the person is in a resting position.

All these kinds of stockings may be called passive, since they give a predetermined compressive force being constant, except for loosing elasticity due to wear. An advantage could be obtained if the compressive forces were controllable in some way. This is the case in U.S. Pat. No. 6,123,681, where the stocking contains polymer of the kind constricting if exposed to some stimulus, preferable electric. By splitting the polymer into a plurality of strips, each being controlled individually, compressive forces may be generated sequentially along the length of the stocking to stimulate fluid flow, such as blood. The power source making the stimulations is then possible programmed in some way, like to make the individual polymer strips constrict in a cyclic order.

SUMMARY OF THE INVENTION

It is a task of this invention to supply an active support for a body extremity such as a leg, which can be used by a person underneath the clothes and will reduce mobility of the patient, so that the actuation elements build into the stocking may operate in a two-way communication, where stimulations are in response to the actual state of the stocking itself, the actuation elements working as sensors too. An alternative possibility is to stimulate in response to signals from some external sensor, perhaps registering the heart rate, the blood flow, body temperature, moist under the stocking due to sweat or other parameters. It is as an example possible to synchronise the actuation of the stocking with the heart rate in such a way that the stocking is relaxed during the systolic period to allow free flow in the arteries, while the contraction takes place during the diastolic period in order to stimulate peristaltic flow in the veins. This task is solved in that an elastic bandage comprises an elastic layer for surrounding a body extremity to exert compressive force on the extremity, where the bandage is, at least partly, formed by elastomeric actuation elements, electrical control of the compressive force being possible.

Elastomeric actuators have recently become known, and exist in different types and based on different principles. One such elastomeric actuator type is known from DE 100 54 247, where a corrugated elastomeric core is supplied with an electrode on each side, vaporised onto basically the whole of the core material in a thin layer. The electrode will follow the corrugation of the core, and hereby provide a higher deformability in a direction crossing the corrugation than in a direction along the corrugation, referred to as compliant electrodes or mechanical anisotropic properties. Placing such elastomeric elements inside or as part of a bandage will provide an elastic bandage that is electrically controllable, if the direction of high deformability is the one surrounding the extremity. The elastomeric actuation elements have the ability that they expand their length when a voltage are applied, unlike U.S. Pat. No. 6,123,681 where the polymers constrict when affected by a stimulation.

In the forthcoming actuation elements is to be understood as any elastic elements able to react due to some stimulation, preferable electric, and elastomeric actuation elements is to be understood as any such systems as mentioned above consisting of an elastomer with electrodes on the top and bottom sides.

In one embodiment of the invention the bandage can be formed as a stocking to be put on the extremity. Hereby is achieved that the bandage can be made with a shape corresponding to the extremity, the compressive force being equally disposed over the whole of the extremity surrounded by the bandage in a not electrically controlled situation.

In another embodiment of the invention the bandage can be formed as a sheet to be wrapped around the extremity. Hereby is achieved that the bandage can be used as an ordinary bandage, on any person and on any extremity, only with the compressive force control as an additional feature. Additionally, it can be achieved that open stockings, like the ones used by athletics as knee-support, can be put on easily by means of band of Velcro TM or a zip that will be properly placed on stockings to allow the stocking to be put on easily. This easily-put-on stocking is disclosed in U.S. Pat. No. 5,520, 630, only without the electrically compressive force control.

In a specific embodiment of the invention the bandage as in U.S. Pat. No. 6,123,681 comprises separate controllable elastomeric actuation elements, formed along the extremity when said bandage is surrounding it, hereby giving the possibility of performing a peristaltic movement along the extremity. Separate controllable elastomeric actuation elements will have the effect that each small area comprising one separate element will be controllable without having any influence on all other areas. Controlling all elements in a one-by-one manner will thus give a peristaltic movement along the bandage, and thus along the extremity.

The object of this invention could further be achieved in that a system for adding compressive force to a body extremity consists of an elastic bandage as previously described and a control unit, the control unit being electrically connected to electrodes on each separate controllable elastomeric actuation element.

In one embodiment of the invention the system could further comprise a sensor capable of producing a signal representative for the blood circulation through the body extremity, or some other parameter like the body temperature or the sweating underneath the stocking. Hereby is achieved that the compressive force on the extremity from the bandage can be measured by the control unit, a compressive force control being obtainable.

Preferably, the control unit is able to supply an adjustable voltage to the electrodes on each separate controllable elastomeric actuation element. Hereby compressive force control of each element can be achieved.

It could be preferable that the control unit adjusts the voltage with reference to the capacitance of each separate controllable elastomeric actuation element. In this embodiment the actuation element operates in two-way communication as both a sensor of a compressive force and an actuator adjusted in response to the voltage of the control unit. Two-way communication is achieved since the compressive force between the two electrodes on each elastomeric element is sensible, and thus controllable, meaning that the force compression on the extremity is roughly sensible, depending on volume variations of the extremity during the day.

In a specific embodiment of the invention the control unit could adjust the voltage in order to obtain a given capacitance of each separate controllable elastomeric actuation element. In a further specific embodiment the given capacity could be adjusted with reference to the sensor, hereby adjusting the compressive force of the elastic bandage with reference to blood circulation through the body extremity. This will provide a bandage system that could be optimised with respect to blood circulation, so that maximum pressure is applied to the extremity without preventing blood circulation to body elements after the extremity in direction from the heart.

BRIEF DESCRIPTION OF THE DRAWINGS

Now having described the invention in general terms a specific embodiment of the invention is to be disclosed with reference to the drawings, showing.

DETAILED DESCRIPTION OF THE PREFERRED EMBODIMENTS

Figure 3:
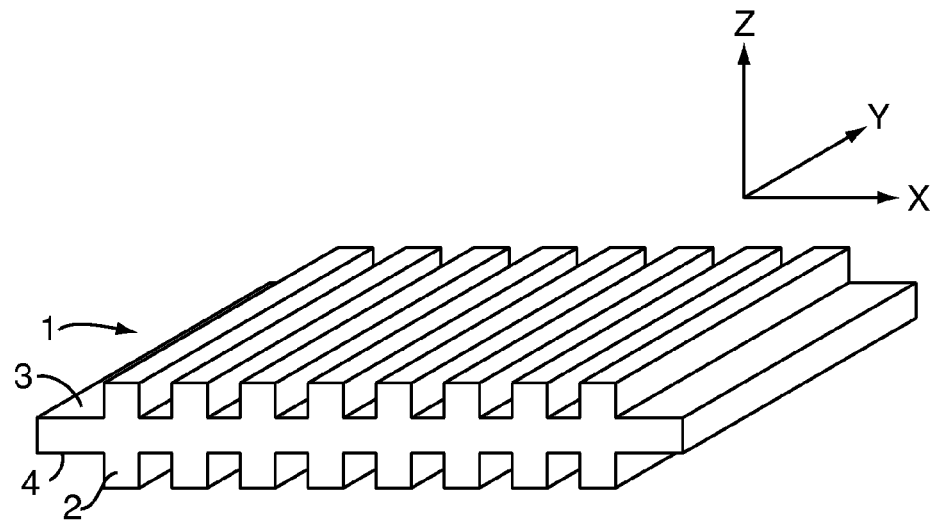
FIG. 3: is a principle view of a corrugated elastomeric element.

FIG. 3 indicates a corrugated elastomeric actuator 1, where the corrugation 2 has a square shape. The corrugation runs in the Y-direction according to the indicated system of co-ordinates, and the X-direction is running across the corrugation. Separate electrodes have been vaporised onto the top surface 3 and the bottom surface 4, whereby an electrical field-can be applied between the two electrodes. When the two electrodes are forced towards each other, due to the electrical field, the elastomeric core material will be squeezed in the Z-direction, and due to volume preservation it will increase in the Z-direction, leading to an increase in the X-direction, the Y-direction or both. The corrugation combined with the electrode will, however, make the X-direction far more deformable than the Y-direction, and the increase will therefore only be in the X-direction. This has previously been referred to as compliant electrodes or mechanical anisotropic properties.

Figure 4:
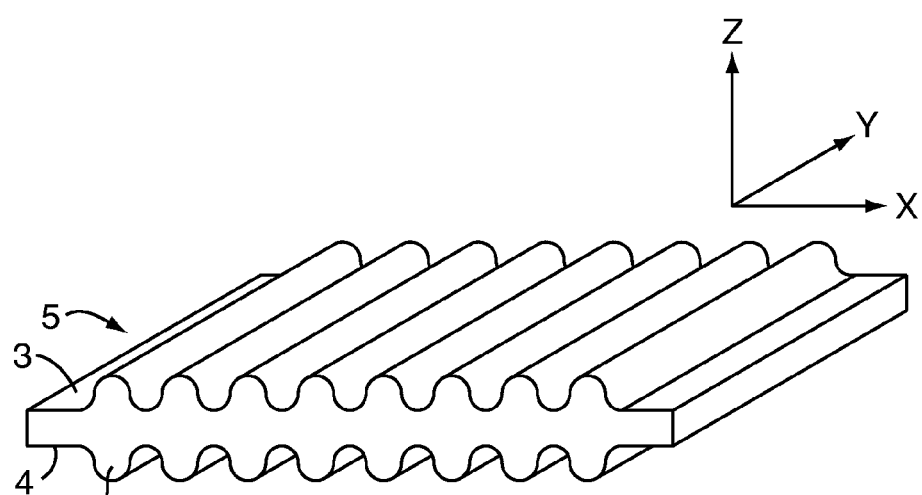
FIG. 4: is a principle view of a corrugated elastomeric element.

The square shaped corrugation is just an example, and in FIG. 4 a wave-shaped corrugation is indicated. The principle is, however, the same, the structure has compliant electrodes or mechanical anisotropic properties.

The force and displacement, which one element from FIG. 3 or 4 is able to deliver, are of course depending on the material and on the level of the electrical field. From U.S. Pat. No. 5,977,685 is it known to laminate more elements together, the laminated stack of elements being able to deliver a force and displacement also depending on the number of elements in the stack, meaning that force and displacement within a large area can be obtained.

Figure 1:
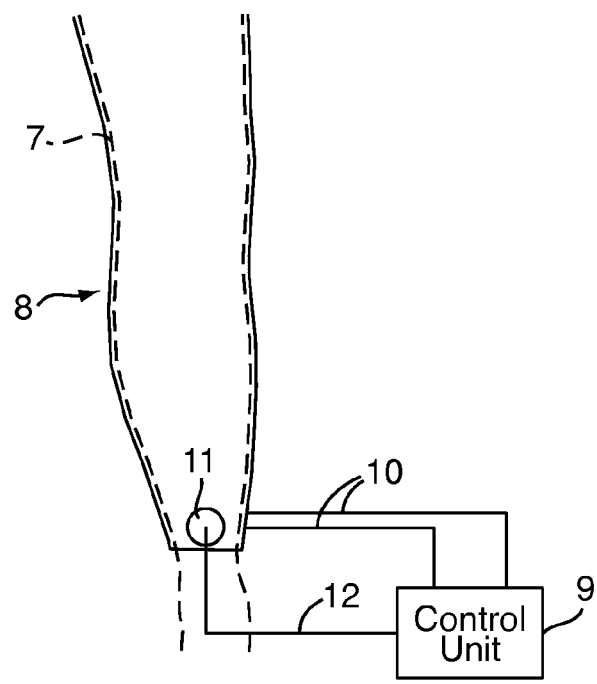
FIG. 1: is a principle view of a bandage with control unit and sensor, the bandage surrounding a body extremity indicated with dotted lines.

An embodiment of the invention is indicated in FIG. 1, where a stocking 8 surrounds a body extremity 7, for example, the lower part of a leg. The stocking is made with elastomeric actuators like the one in FIGS. 3 and 4, and the electrodes of all actuators are connected in parallel inside the stocking, and only two electrodes 10 are lead from the stocking to a control unit 9. The control unit comprises a battery, by means of which an electrical field is applied to the electrodes of all actuators. The level of the electrical field is controlled by controlling the level of the voltage supplied from the control unit 9 to the electrodes, and the level of the voltage is controlled in accordance with a signal from a sensor 11, which communicates a signal corresponding to the blood circulation through the extremity 7 to the control unit via the connection 12.

Figure 2:
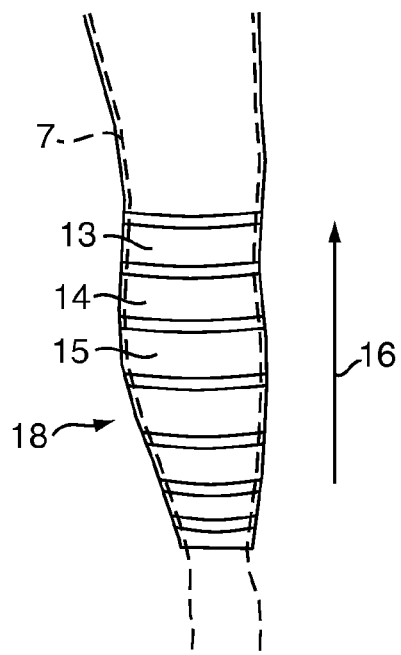
FIG. 2: is a principle view of a bandage, made with separate controllable elastomeric elements.

FIG. 2 indicates a specific embodiment of the invention. The stocking 18 is surrounding the extremity 7, and the elastomeric actuators are placed in bands 13, 14, 15 and so on. Each band 13, 14, 15 is individually controllable from a control unit not shown in FIG. 2. This means that a peristaltic movement in the direction indicated by the arrow 16 can be made simply by adding a compressive force to the bands one by one. As an example, a compressive force should be added to band 15, then to band 14, then to band 13 and so on.

While the present invention has been illustrated and described with respect to a particular embodiment thereof, it should be appreciated by those of ordinary skill in the art that various modifications to this invention may be made without departing from the spirit and scope of the present invention.

The invention claimed is:

1. An electro-active compression bandage system comprising:
    a bandage having an elastic layer for surrounding a body extremity to exert compressive force on said extremity, and being at least partly formed by actuation elements that are controllable in their compressive force when stimulated, wherein said compressive force is at least roughly sensible, so that said actuation elements may operate in a two-way communication, also operating as sensors of their own actual state of compressive force, and wherein said bandage is, at least partly, formed by elastomeric actuation elements containing electrodes on the top and bottom surfaces, electrical control of the compressive force being possible.

2. The system according to claim 1, wherein the top and bottom surfaces of the elastomeric actuation elements are corrugated.

3. The system according to claim 2, wherein changing a capacitance does said adjustment of the compressive force.

4. The system according to claim 3, wherein said signal from said control unit is a voltage.

5. The system according to claim 4, wherein said control unit adjusts said signal in order to keep a given constant capacitance of each separate controllable actuation element.

6. An electro-active compression bandage system comprising:
- an elastic bandage having an elastic layer for surrounding a body extremity to exert compressive force on said extremity, and being at least partly formed by actuation elements controllable in their compressive force when stimulated, wherein said compressive force is at least roughly sensible, so that said actuation elements may operate in a two-way communication, also operating as sensors of their own actual state of compressive force, wherein said bandage is, at least partly, formed by actuation elements, wherein said actuation elements will reduce the compressive forces when activated by stimulation; and
- a control unit regulating the compressive force of the actuation elements,
- wherein the control unit adjusts the compressive force with reference to the actual state of each controllable actuation element, and
- wherein said elastic bandage includes actuation elements placed in bands, and wherein said control unit is able to supply an individual adjustable stimulation to each separate actuation element band.

7. An electro-active compression bandage system comprising:
- an elastic bandage having an elastic layer for surrounding a body extremity to exert compressive force on said extremity, and being at least partly formed by actuation elements controllable in their compressive force when stimulated;
- wherein said compressive force is at least roughly sensible, so that said actuation elements may operate in a two-way communication, also operating as sensors of their own actual state of compressive force;
- wherein said bandage is, at least partly, formed by elastomeric actuation elements including electrodes on the top and bottom surfaces, electrical control of the compressive force being possible;
- wherein the top and bottom surfaces of the elastomeric actuation elements are corrugated; and
- wherein changing a capacitance does said adjustment of the compressive force.

8. The system according to claim 7, wherein said signal from said control unit is a voltage.

9. The system according to claim 8, wherein said control unit adjusts said signal in order to keep a given constant capacitance of each separate controllable actuation element.

10. An electro-active compression bandage system comprising:
- a bandage having an elastic layer for surrounding a body extremity to exert compressive force on said extremity, and being at least partly formed by actuation elements that are controllable in their compressive force when stimulated,
- wherein said compressive force is at least roughly sensible, so that said actuation elements may operate in a two-way communication, also operating as sensors of their own actual state of compressive force, and
- wherein said bandage is, at least partly, formed by actuation elements containing electrodes on the top and bottom surfaces, electrical control of the compressive force being possible.

* * * * *